United States Patent
Maginot et al.

(10) Patent No.: US 6,190,371 B1
(45) Date of Patent: Feb. 20, 2001

(54) CATHETER SYSTEM HAVING RETRACTABLE WORKING CATHETER AND ASSOCIATED METHOD

(75) Inventors: Paul J. Maginot, Fishers; Thomas J. Maginot, Crown Point, both of IN (US)

(73) Assignee: Maginot Vascular Systems, Crown Point, IN (US)

(*) Notice: Under 35 U.S.C. 154(b), the term of this patent shall be extended for 0 days.

(21) Appl. No.: 09/246,831

(22) Filed: Feb. 8, 1999

Related U.S. Application Data

(60) Provisional application No. 60/116,017, filed on Jan. 15, 1999.

(51) Int. Cl.$^7$ .................................................. A61M 25/00
(52) U.S. Cl. ........................... 604/523; 604/264; 604/171
(58) Field of Search .................................. 604/263, 264, 604/265, 269, 43, 275, 280, 523, 171, 158, 905, 921, 206, 533, 165.01, 165.02; 285/120.1, 121.1, 121.2, 123.1, 302

(56) References Cited

U.S. PATENT DOCUMENTS

| | | | |
|---|---|---|---|
| 2,448,232 | * | 8/1948 | Muse ....................................... 285/11 |
| 4,266,999 | * | 5/1981 | Baier ..................................... 156/227 |
| 4,468,216 | | 8/1984 | Muto . |
| 4,493,696 | | 1/1985 | Uldall . |
| 4,738,667 | | 4/1988 | Galloway . |
| 4,900,202 | | 2/1990 | Wienhold . |
| 5,013,194 | | 5/1991 | Weinhold . |
| 5,053,023 | | 10/1991 | Martin . |
| 5,156,592 | | 10/1992 | Martin et al. . |
| 5,236,424 | | 8/1993 | Imran . |
| 5,261,416 | * | 11/1993 | Taussig ................................ 604/171 |
| 5,405,320 | * | 4/1995 | Twardowski et al. .................. 604/43 |

(List continued on next page.)

OTHER PUBLICATIONS

Marketing brochure entitled "Uldall Double Lumen Hemodialysis Catheter Trays", Cook Critical Care, A Division of Cook Incorporated, P.O. Box 489, Bloomington, Indiana 47402, 1994.

Interventional Radiology, vol. One, Second Edition, Published by Williams & Wilkins, 428 East Preston Street, Baltimore, Maryland 21202, pp. 366–367: 1992.

Marketing brochure from Micro Therapeutics, Inc. 1062–F Calle Negocio, San Clemente, California 92673.

Marketing brochure entitled "Bard Access Systems Hickman ®: Hemodialysis/Plasmapheresis Catheter", Bard Access Systems, Hickman, Groshong, Designs for Life™, 5425 West Amelia Earhart Drive, Salt Lake City, Utah 84116.

*Primary Examiner*—Wynn Wood Coggins
*Assistant Examiner*—Jennifer Maynard
(74) *Attorney, Agent, or Firm*—Paul J. Maginot

(57) ABSTRACT

A catheter system includes a multi-lumen working catheter having a first distal working orifice and a second distal working orifice. The catheter system further includes a guide catheter having a guide lumen and a distal guide orifice. Also, the catheter system includes a locking mechanism which locks the working catheter relative to the guide catheter in (i) an operative position, and (ii) a stowed position. When the working catheter is locked in the operative position, (i) the working catheter extends through the guide lumen of the guide catheter and out of the distal guide orifice of the guide catheter, and (ii) the first distal working orifice and the second distal working orifice are each positioned outside of the guide catheter. Additionally, when the working catheter is locked in the stowed position, (i) the working catheter extends into the guide lumen of the guide catheter, and (ii) the first distal working orifice and the second distal working orifice are each positioned within the guide lumen of the guide catheter. A method of performing dialysis with a catheter system is also disclosed.

4 Claims, 10 Drawing Sheets

U.S. PATENT DOCUMENTS

| | | |
|---|---|---|
| 5,405,323 | 4/1995 | Rogers et al. . |
| 5,417,669 | 5/1995 | Castaneda et al. . |
| 5,470,180 | 11/1995 | Jore . |
| 5,498,240 | 3/1996 | Bagaoisan et al. . |
| 5,514,112 | 5/1996 | Chu et al. . |
| 5,569,182 | 10/1996 | Twardowski et al. . |
| 5,569,204 | 10/1996 | Cramer . |
| 5,591,138 * | 1/1997 | Vaillaincourt ........................ 604/263 |
| 5,779,404 | 7/1998 | Jore . |
| 5,971,958 * | 10/1999 | Zhang ................................ 604/164 |

* cited by examiner

CATHETER SYSTEM HAVING RETRACTABLE WORKING CATHETER AND ASSOCIATED METHOD

REFERENCE TO PROVISIONAL PATENT APPLICATION

This application claims the benefit of U.S. Provisional Application Ser. No. 60/116,017 filed Jan. 15,1999.

CROSS REFERENCE

Cross reference is made to U.S. patent application Ser. No. 09/078,834, now U.S. Pat. No. 5,989,213, entitled "Long-Term Dialysis Catheter System and Associated Method" by Thomas J. Maginot filed on May 14, 1998.

BACKGROUND OF THE INVENTION

The present invention relates generally to catheters, and more particularly to a catheter system for use in a body of a patient and an associated method which maintains fluid flow in the catheter system.

Various medical procedures require that a patient be catheterized. For example, catheterization may be required when a patient undergoes hemodialysis or has a clot aspirated from a blood vessel. Generally, the length of time the patient will be catheterized dictates whether a physician will utilize a "temporary catheterization technique" (i.e. a technique in which the catheter is left in a blood vessel for a relatively short period of time such as a few minutes, hours, days, or weeks) or a "permanent catheterization technique" (i.e. a technique in which the catheter is left in a blood vessel for a relatively long period of time such as several months or indefinitely).

For example, a procedure in which a clot is aspirated from a blood vessel typically includes placing the catheter in the blood vessel for a relatively short period of time such as a few minutes to a few hours and then withdrawing the catheter once the clot has been removed. Therefore, when performing such an aspiration procedure, it is common for a physician to use the temporary catheterization technique to place the catheter in the blood vessel of the patient.

On the other hand, when a procedure is performed to effect hemodialysis, a physician may place a catheter in the blood vessel for a relatively long period of time. In particular, a patient suffering from kidney failure who is involved in a hemodialysis regimen typically requires a dialysis session three days per week for an indefinite period of time whereby extra fluid, chemicals, and wastes are removed from his/her body. A patient who is involved in such a hemodialysis regimen may need a catheter placed in his/her blood vessel for a relatively long period of time in order to provide a ready means for vascular access into his/her bloodstream over such relatively long period of time. This long term placement of the catheter for dialysis purposes may be desirable for a number of reasons.

Firstly, a patient may have experienced progressive loss of other conventional long term vascular access possibilities such as surgically created arteriovenous fistulas. Accordingly, the long term placement of the catheter in the patient's blood vessel may be the best alternative for the patient as he/she proceeds with the hemodialysis regimen.

Additionally, the long term placement of the catheter in the patient's blood vessel may be desirable after initial creation of an arteriovenous fistula in the patient's body. In particular, it is desirable to provide a ready means for vascular access into the patient's bloodstream during a maturation period of the arteriovenous fistula. The maturation period allows the arteriovenous fistula to develop sufficiently so that it will function as a ready means for vascular access into the patient's bloodstream which may be safely punctured multiple times per week for hemodialysis. The length of time of this maturation period is typically on the order of several weeks (e.g. three weeks) to many months (e.g. six months).

Therefore, when performing a hemodialysis procedure, it is common for a physician to use the permanent catheterization technique to place the catheter in the blood vessel of the patient.

These two catheterization techniques are significantly different with respect to their complexity and degree of invasiveness. For example, in the case of the temporary catheterization technique, it is common to insert a temporary catheter into a patient's blood vessel using a "direct puncture technique." This technique entails creating a small incision in a patient's skin with a scalpel directly over the blood vessel to be catheterized. A needle is then advanced through the skin incision and subcutaneous tissue and into the blood vessel. Thereafter, a guidewire is advanced through the needle into the blood vessel and the needle is subsequently removed over the guidewire. Then, one or more tubular vessel dilators are used to widen the opening defined in the skin and subcutaneous tissue, and further to widen the opening defined in the blood vessel wall to a caliber similar to that of the temporary catheter. The temporary catheter is then advanced over the guidewire and into the blood vessel. Thereafter, the guidewire is removed.

When the temporary catheterization technique is used during a clot aspiration procedure, two catheters are usually placed in the blood vessel of a patient. In particular, an outer catheter is usually placed within the blood vessel using the above described direct puncture technique so that its distal orifice is located near the clot. Thereafter, an inner catheter having a smaller caliber relative to the outer catheter is advanced through a lumen of the outer catheter. While the inner catheter is positioned within the outer catheter, an aspiration vacuum is applied to the inner catheter with a syringe. If the size of the clot (or fragments thereof) are smaller than the inner diameter of the inner catheter, then the clot or clot fragments are drawn into and through the inner catheter thereby removing the clot from the blood vessel. If the size of the clot or clot fragments are larger than the inner diameter of the inner catheter, then the clot or clot fragments are drawn to a location adjacent to the distal orifice of the inner catheter. Subsequently, while the aspiration vacuum is still being applied, the inner catheter is withdrawn from the outer catheter thereby additionally withdrawing the clot or clot fragments from the outer catheter and the patient's blood vessel. Thereafter, the outer catheter remains temporarily in place within the blood vessel of the patient for subsequent injections of radiographic contrast for imaging purposes to determine the extent of clot remaining in the blood vessel as well as to determine if clot has migrated to another location within the blood vessel. The outer catheter, which remains temporarily in place in the blood vessel, provides a conduit for the inner catheter to be advanced back into the patient's blood vessel for additional aspiration attempts which are usually required for complete removal of the clot from the blood vessel.

If an outer catheter needs to be replaced during a clot aspiration procedure because of catheter malfunction, such replacement can be accomplished by advancing a guidewire through the lumen of the outer catheter and into the blood vessel. The existing outer catheter can then be removed over the guidewire to a location outside of the patient's body. Thereafter, a new outer catheter is placed in the patient's blood vessel by advancing the new outer catheter over the guidewire as discussed above.

In contrast to the temporary catheterization technique, the permanent catheterization technique typically entails inserting a permanent catheter into a patient's blood vessel using a "tunneled catheter technique." The tunneled catheter technique includes (i) creating a first opening by making a small incision in a patient's skin with a scalpel directly over the blood vessel to be catheterized, (ii) puncturing the blood vessel at a location directly below the first opening by advancing a needle through the skin incision and subcutaneous tissue and into the blood vessel, (iii) advancing a guidewire through the needle into the blood vessel, (iv) removing the needle over the guidewire, (v) passing one or more tubular vessel dilators over the guidewire to widen the opening defined in the skin and subcutaneous tissue, and further to widen the opening defined in the blood vessel wall to a caliber similar to that of the tubular guide, (vi) advancing the tubular guide over the guidewire and into the blood vessel, (vii) thereafter, creating a second opening in the patient's skin spaced apart at least several centimeters from the first opening, (viii) advancing a tunneling instrument from the second opening to the first opening so as to create a passageway within the subcutaneous tissue under the skin between the first opening and the second opening, (ix) advancing a permanent catheter having a tissue ingrowth member attached to an outer surface thereof into the second opening and through the passageway such that a distal end of the permanent catheter is located adjacent the first opening, (x) inserting the distal end of the permanent catheter through the tubular guide member and into the blood vessel to be catheterized whereby the tissue ingrowth member is positioned in the subcutaneous tissue, (xi) removing the tubular guide member, and (xii) closing the first opening with suture whereby the permanent catheter (a) is no longer exposed through the first opening, (b) extends for at least several centimeters under the patient's skin between the second opening and the location where the permanent catheter enters the blood vessel, and (c) extend outs of the second opening so that a proximal end of the permanent catheter is located outside of the patient's body.

In contrast to the direct puncture catheter technique, the tunneled catheter technique results in the placement of a catheter in a patient's body in a manner which allows the catheter to remain safely in the patient's body for a relatively long period of time. For example, a degree of safety is achieved by separating the following two openings by at least several centimeters: (i) the skin opening through which the catheter enters the patient's body, and (ii) the blood vessel opening through which the catheter enters the patient's vascular system. This safety feature decreases the likelihood that bacteria will migrate up the length of the catheter from the skin opening and cause an infection at the blood vessel opening.

In addition, another degree of safety is achieved by providing a tissue ingrowth member which is attached to and extends around an outer surface of the catheter. As the catheter is left in the patient's body over a period of time, the tissue ingrowth member becomes affixed to the subcutaneous tissue of the patient's body thereby providing a secure attachment of the catheter to the patient's body. Providing a secure attachment between the catheter and the patient's body reduces the likelihood that the catheter will be inadvertently removed or withdrawn from the patient's body. Moreover, since the subcutaneous tissue becomes attached to the tissue ingrowth member, a physical barrier is created between following two openings: (i) the skin opening through which the catheter enters the patient's body, and (ii) the blood vessel opening through which the catheter enters the patient's vascular system. This physical barrier further decreases the likelihood that bacteria will migrate up the length of the catheter from the skin opening and cause an infection at the blood vessel opening.

While the tunneled catheter technique provides the significant advantage of allowing the catheter to remain safely in the patient's body for a relatively long period of time, significant disadvantages of the tunneled catheter technique exists. For example, when a catheter remains in a blood vessel for a long period of time, there is a tendency for blood clots including fibrin (e.g. in the form of a fibrin sheath) to attach to and build-up on the outer and inner surfaces of the portion of the catheter which is located within the blood vessel. The above described attachment and build-up tends to occlude the various distal orifices defined in the catheter which enable fluid movement into and out of the catheter. For instance, attempts at withdrawing blood through the catheter may be unsuccessful due to blood clots creating a "ball-valve" effect which occlude the various distal orifices of the catheter.

When occlusion of the various distal orifices of the catheter occurs due to the above described blood clot attachment and build-up, a physician has several options for eliminating the occlusion thereby reestablishing access to the vascular system. One option is to remove the occluded catheter and replace it with a new catheter. However, in contrast to the ease of exchanging a catheter which was placed in the patient's body using the direct puncture technique, exchanging a catheter which was placed in the patient's body using the tunneled catheter technique is substantially more complicated and invasive. This is true since in order to remove the occluded catheter from the patient's body, the physician must surgically dissect the tissue ingrowth member which is secured to the outer surface of the catheter from the patient's subcutaneous tissue. Recall that the tissue ingrowth member becomes affixed to the subcutaneous tissue over a period of time. Thereafter, the physician would place a new catheter into the patient's body generally using the above described tunneled catheter technique. Therefore, this option is undesirable since it requires additional surgery which further traumatizes the patient and increases the cost of the medical care.

Another option for eliminating the occlusion of the various distal orifices of the catheter in order to reestablish access to the vascular system involves the performance of a medical procedure in which a blood clot-dissolving medication such as urokinase is infused into the catheter. However, this medication is not always successful in eliminating the occlusion of the various distal orifices of the catheter. In addition, infusion of the medication into the catheter subjects the patient to potential bleeding complications due to the medication entering the vascular system and being circulated systemically. Further, this medication is expensive. Thus, this option has serious drawbacks as well.

An additional option for eliminating the occlusion of the various distal orifices of the catheter in order to reestablish access to the vascular system involves the performance of a medical procedure in which an intravascular snare is introduced into the blood vessel in order to physically strip off any blood clots or fibrin sheath which has attached and built-up on the distal portion of the catheter. However, for catheters placed in veins, this medical procedure requires a venopuncture in the femoral or jugular vein which is invasive and can be uncomfortable for a patient. Furthermore, this option requires the use of (i) an intravascular snare, (ii) a physician experienced in catheter techniques, and (iii) an angiographic suite to provide fluoroscopic imaging. Use of each of items (i), (ii), and (iii) above causes this option to be relatively expensive. Consequently, this option also has significant disadvantages.

What is needed therefore is a method and apparatus which reduces the likelihood of occlusion of the various distal orifices of a catheter which has been placed in a patient's body using the tunneled catheter technique which overcomes one or more of the above-mentioned drawbacks.

SUMMARY OF THE INVENTION

In accordance with one embodiment of the present invention, there is provided a catheter system which includes a working catheter having a distal working orifice. The catheter system further includes a guide catheter having a guide lumen and a distal guide orifice. The catheter system additionally includes a locking mechanism which locks the working catheter relative to the guide catheter in (i) an operative position, and (ii) a stowed position. When the working catheter is locked in the operative position, (i) the working catheter extends through the guide lumen of the guide catheter and out of the distal guide orifice of the guide catheter, and (ii) the distal working orifice of the working catheter is positioned outside of the guide catheter. When the working catheter is locked in the stowed position, (i) the working catheter extends into the guide lumen of the guide catheter, and (ii) the distal working orifice of the working catheter is positioned within the guide lumen of the guide catheter.

Pursuant to another embodiment of the present invention, there is provided a method of performing dialysis with a catheter system which includes (i) a working catheter having a distal working orifice, and (ii) a guide catheter having a guide lumen and a distal guide orifice. The method includes the step of locking the working catheter in an operative position in which (i) the working catheter extends through the guide lumen of the guide catheter and out of the distal guide orifice of the guide catheter, and (ii) the distal working orifice of the working catheter is positioned outside of the guide catheter. The method further includes the step of advancing and withdrawing blood through the working catheter while the working catheter is locked in the operative position. Also, the method includes the step of locking the working catheter in a stowed position in which (i) the working catheter extends into the guide lumen of the guide catheter, and (ii) the distal working orifice of the working catheter is positioned within the guide lumen of the guide catheter.

According to still another embodiment of the present invention, there is provided a method of performing a medical procedure with a catheter system which includes (i) a working catheter having a distal working orifice, and (ii) a guide catheter having a guide lumen and a distal guide orifice. The method includes the step of locking the working catheter in an operative position in which (i) the working catheter extends through the guide lumen of the guide catheter and out of the distal guide orifice of the guide catheter, and (ii) the distal working orifice of the working catheter is positioned outside of the guide catheter. Moreover, the method includes the step of advancing and withdrawing fluid through the working catheter while the working catheter is locked in the operative position. The method also includes the step of locking the working catheter in a stowed position in which (i) the working catheter extends into the guide lumen of the guide catheter, and (ii) the distal working orifice of the working catheter is positioned within the guide lumen of the guide catheter.

In accordance with yet another embodiment of the present invention, there is provided a catheter system which includes a multi-lumen working catheter having a first distal working orifice and a second distal working orifice. The catheter system further includes a guide catheter having a guide lumen and a distal guide orifice. Also, the catheter system includes a locking mechanism which locks the working catheter relative to the guide catheter in (i) an operative position, and (ii) a stowed position. When the working catheter is locked in the operative position, (i) the working catheter extends through the guide lumen of the guide catheter and out of the distal guide orifice of the guide catheter, and (ii) the first distal working orifice and the second distal working orifice are each positioned outside of the guide catheter. Additionally, when the working catheter is locked in the stowed position, (i) the working catheter extends into the guide lumen of the guide catheter, and (ii) the first distal working orifice and the second distal working orifice are each positioned within the guide lumen of the guide catheter.

It is therefore an object of the present invention to provide a new and useful catheter system for use in a body of a patient.

It is also an object of the present invention to provide a new and useful long-term catheter system for use in a body of a patient.

It is another object of the present invention to provide an improved long-term catheter system for use in a body of a patient.

It is yet another object of the present invention to provide a new and useful method of performing dialysis with a catheter system.

It is still another object of the present invention to provide an improved method of performing dialysis with a catheter system.

Other objects and benefits of the present invention can be discerned from the following description and accompanying drawings.

DESCRIPTION OF THE PREFERRED EMBODIMENT

Figure 1:
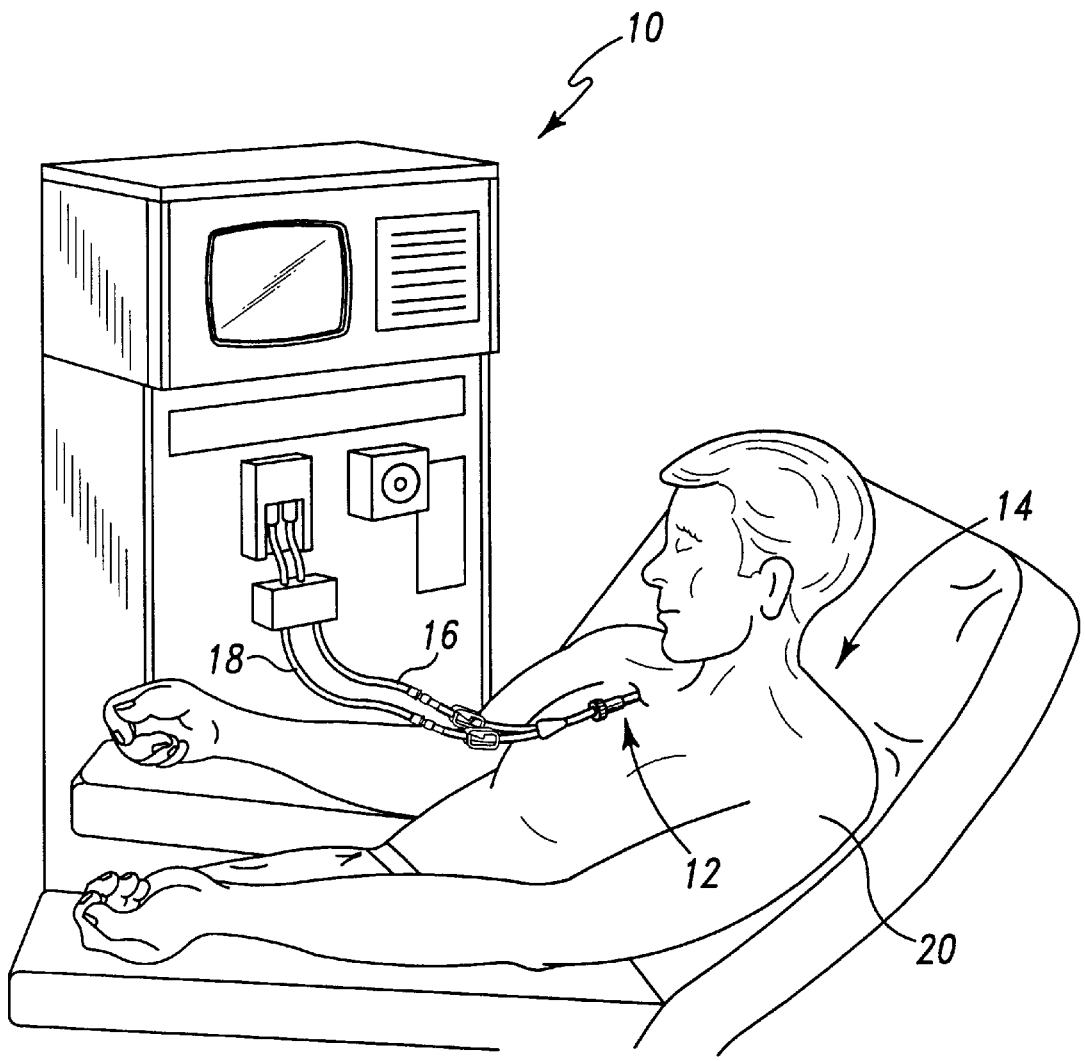
FIG. 1 is a perspective view of a patient undergoing a dialysis procedure utilizing the catheter system of the present invention.

While the invention is susceptible to various modifications and alternative forms, a specific embodiment thereof has been shown by way of example in the drawings and will herein be described in detail. It should be understood, however, that there is no intent to limit the invention to the particular form disclosed, but on the contrary, the intention is to cover all modifications, equivalents, and alternatives falling within the spirit and scope of the invention as defined by the appended claims.

Figure 9:
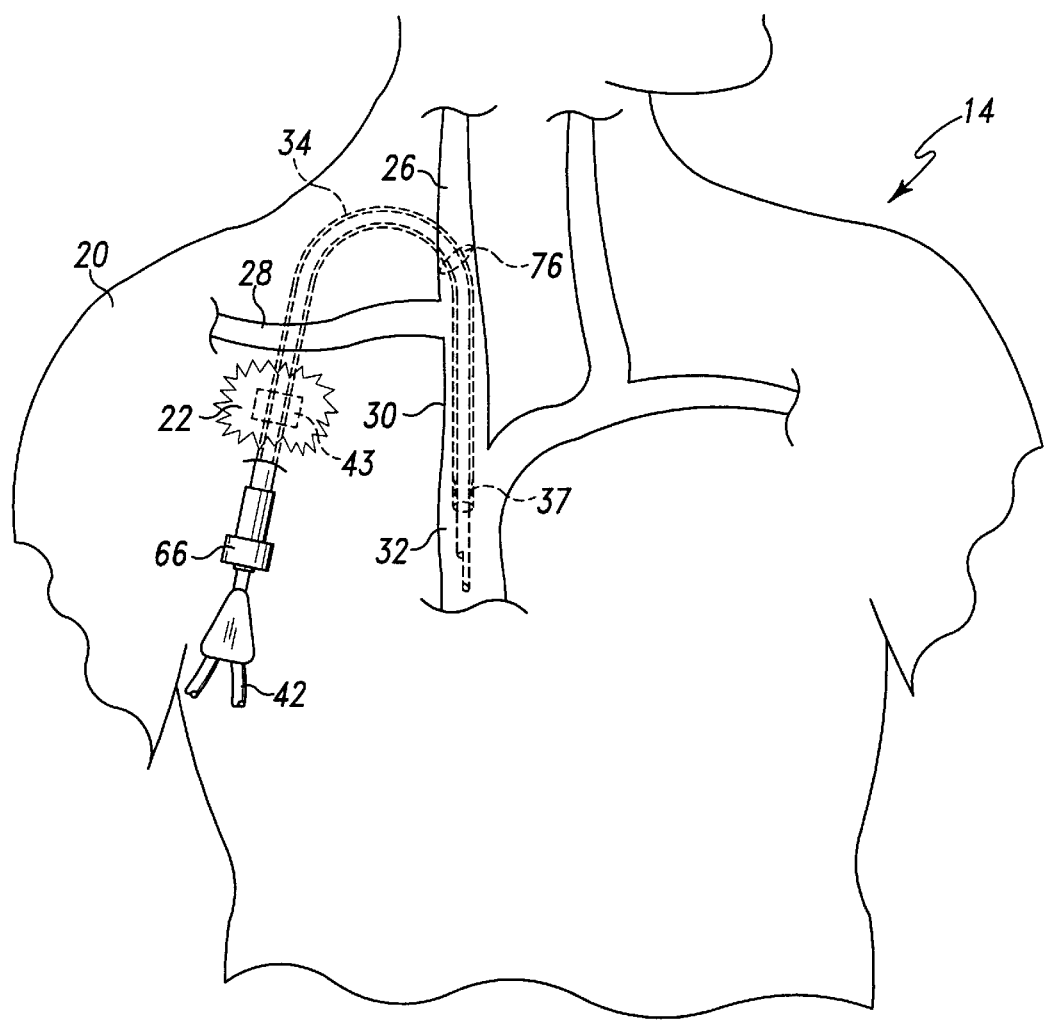
FIG. 9 is an enlarged view which is similar to FIG. 2, but showing the catheter system (i) extending from the right upper chest, (ii) tunneled under the skin within the subcutaneous tissue of the patient for a distance, (iii) entering a venotomy in the right internal jugular vein, and (iv) passing caudally in the right internal jugular vein, the right inominate vein and the superior vena cava.

Referring now to FIG. 1, there is shown a hemodialysis machine 10 to which is attached a long-term catheter system 12 which incorporates the features of the present invention therein. The catheter system 12 is inserted in a patient's body 14. The hemodialysis machine 10 includes an inlet line 16 and an outlet line 18 which are each in fluid communication with the catheter system 12. The body 14 includes skin, generally indicated by the reference numeral 20. The body 14 further includes subcutaneous tissue 22 positioned below the skin 20 (see FIG. 9).

Figure 2:
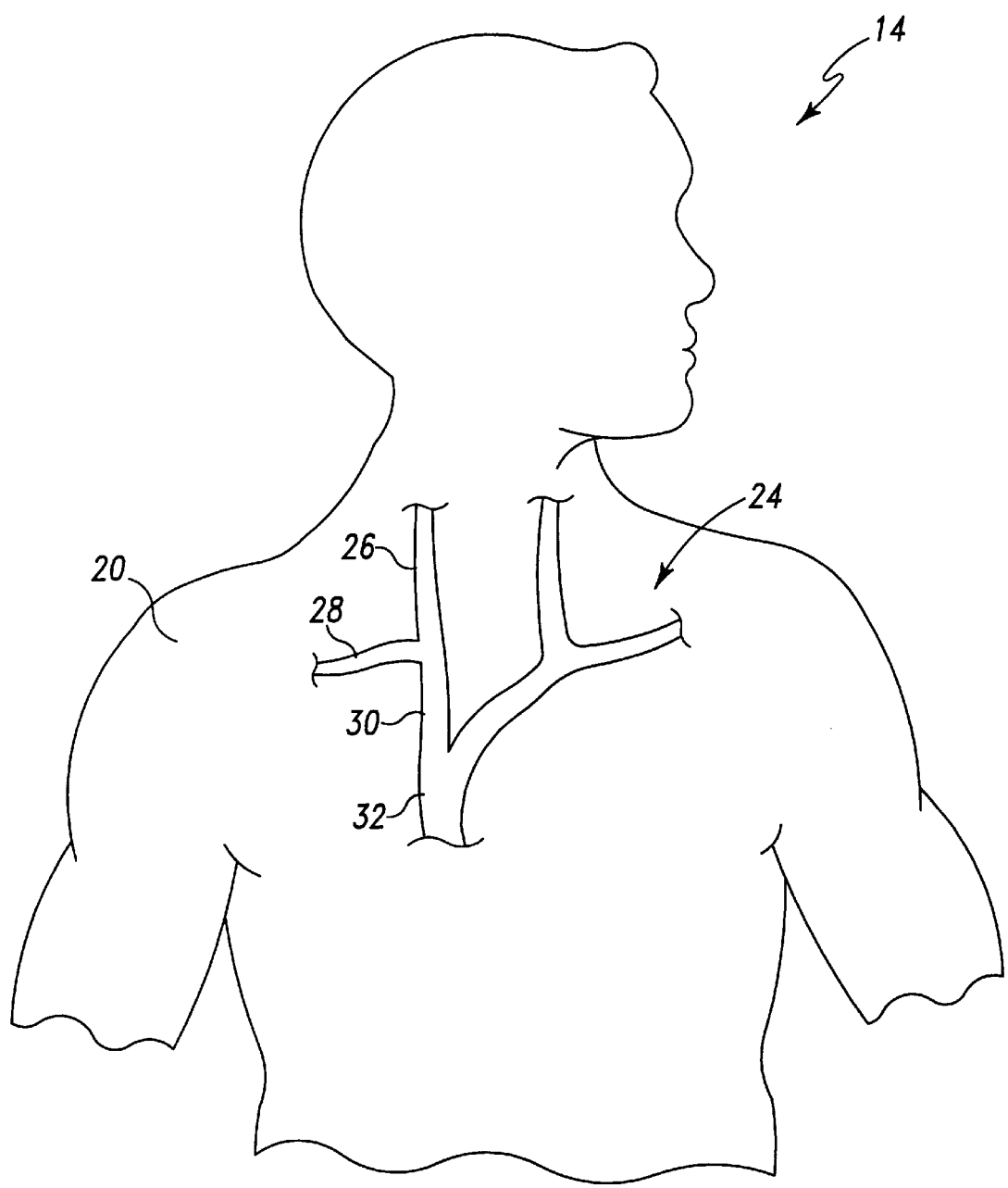
FIG. 2 is a schematic view of a portion of the vascular system of the patient of FIG. 1, showing the right internal jugular vein, the right subclavian vein, the right inominate vein, and the superior vena cava.

As shown in FIG. 2, the body 14 further includes a vascular system 24. The vascular system 24 includes a right internal jugular vein 26, a right subclavian vein 28, a right inominate vein 30, and a superior vena cava 32. Note that the vascular system 24 is positioned within the body 14 underneath the skin 20. However, the vascular system 24, including the right internal jugular vein 26, the right subclavian vein 28, the right inominate vein 30, and the superior vena cava 32, are depicted in FIGS. 2 and 9–11 with solid lines for clarity of description.

Figure 3:
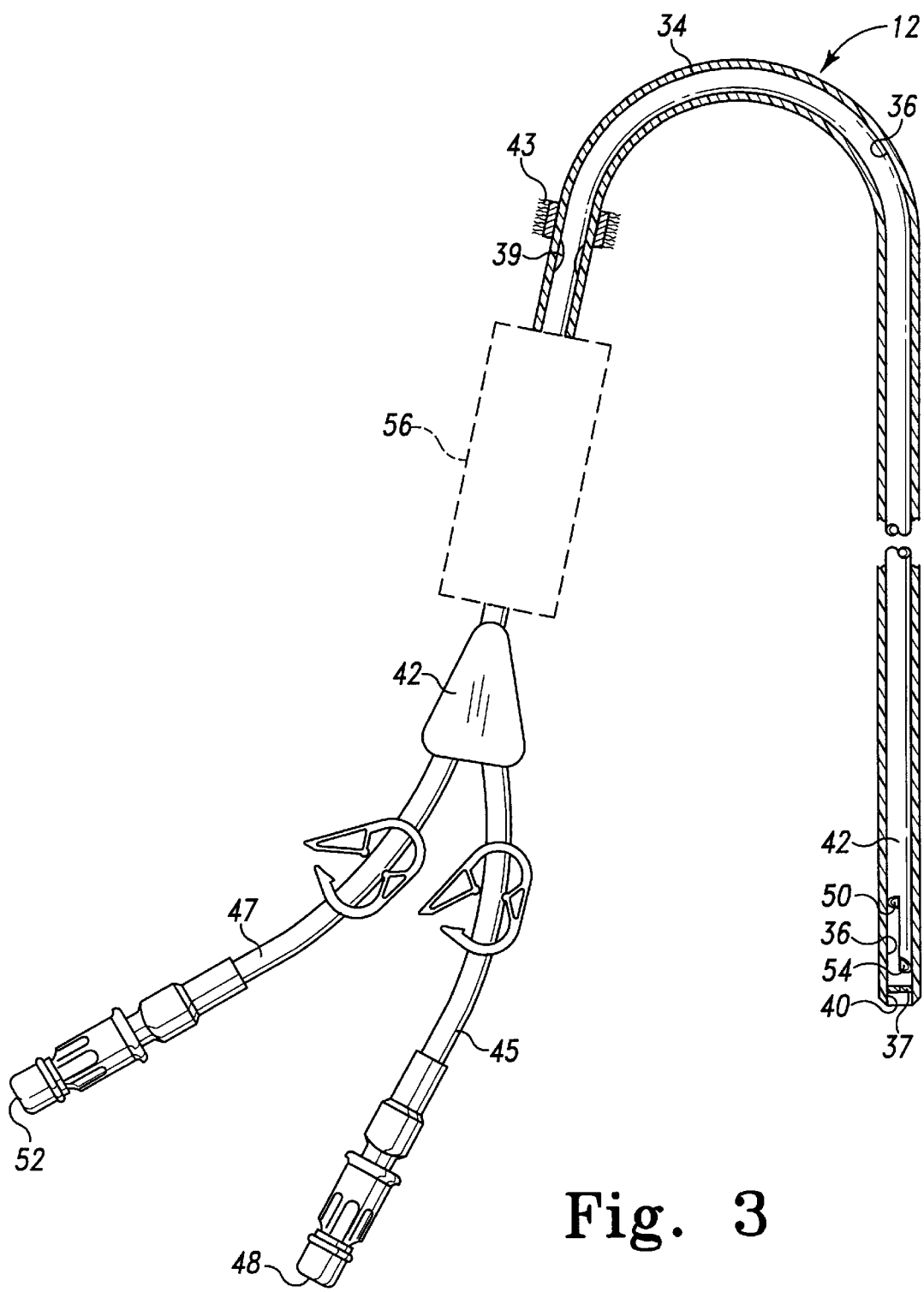
FIG. 3 is an enlarged side elevational view of the catheter system of FIG. 1, showing the working catheter positioned within the guide lumen of the guide catheter, and further schematically showing the locking mechanism which is configured to lock the working catheter relative to the guide catheter in any one of a plurality of positions (note that FIG. 3 shows the locking mechanism operating to lock the working catheter in the stowed position)

The catheter system 12 is shown in more detail in FIG. 3. In particular, the catheter system includes a guide catheter 34 having a central guide lumen 36 which extends the entire length thereof (see also FIGS. 6A–6D). The guide lumen 36 defines a proximal guide orifice 38 and a distal guide orifice 40.

A distal valve 37 is secured to the guide catheter 34 at a location within the guide lumen 36 substantially adjacent to the distal guide orifice 40 (see e.g. FIGS. 3–5, 6A and 6C). The distal valve 37 is configured to inhibit fluid from advancing through the distal guide orifice 40 and past the distal valve 37 within the guide lumen 36 of the guide catheter 34. A proximal valve 39 is also secured to the guide catheter 34 at a location within the guide lumen 36 (see FIGS. 6A, 6B, and 8). The proximal valve 39 is configured to inhibit fluid from advancing within the guide lumen 36 from one side of the proximal valve 39 to the other side of the proximal valve 39. The valves 37, 39 also function to inhibit air flow leakage though the guide lumen 36 of the guide catheter 34. One valve which may be used as either the distal valve 37 or the proximal valve 39 with some modifications is available from Micro Therapeutics, Inc. of San Clemente, Calif. under the trademark "Cragg MicroValve™".

Referring again to FIGS. 6A–6D, the guide catheter 34 also includes an outer surface 41 having a tissue ingrowth member 43 secured thereto. Tissue ingrowth member 43 is configured to facilitate fibrous tissue growth therein. More specifically, the subcutaneous tissue 22 of the body 14 becomes affixed to the tissue ingrowth member 43 when the tissue ingrowth member 43 remains in contact with the subcutaneous tissue 22 over a period of time. One type of tissue ingrowth member which may be used as the tissue ingrowth member 43 is a DACRON cuff which is available from Bard Access Systems of Salt Lake City, Utah.

The catheter system 12 further includes a working catheter 42 which is positioned within the guide lumen 36 of the guide catheter 34 (see FIGS. 3–5 and 10–11). The working catheter 42 has an ingress lumen 44 through which fluid may be advanced, and an egress lumen 46 also through which fluid may be advanced (see FIGS. 7A–7D). The ingress lumen 44 defines a first distal working orifice 50, while the egress lumen 46 defines a second distal working orifice 54. The first distal working orifice 50 and the second distal working orifice 54 are defined in a distal working segment 55 of the working catheter 42 (see FIGS. 4, 5, and 7A).

The working catheter 42 further includes an ingress line 45 and an egress line 47. The ingress line 45 defines a first proximal working orifice 48, while the egress line 47 defines a second proximal working orifice 52. The ingress line 45 is in fluid communication with the ingress lumen 44, while the egress line 47 is in fluid communication with the egress lumen 46. The egress line 47 has an adapter 58 attached thereto, and the ingress line 45 has an adapter 60 attached thereto (see FIG. 7A).

Figure 7A:
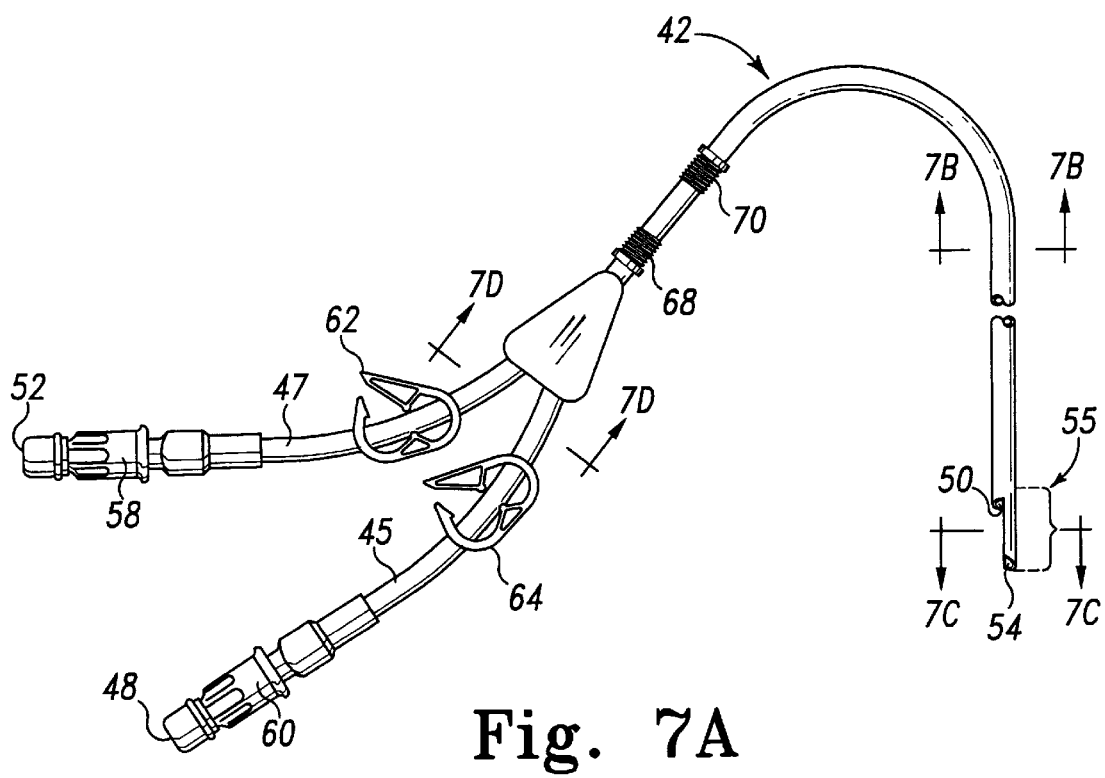
FIG. 7A is an enlarged side elevational view of the working catheter of the catheter system shown in FIG. 1.
Figure 7B:
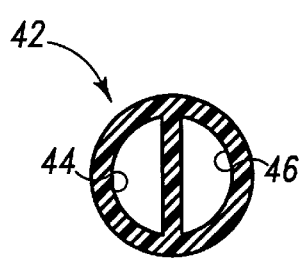
FIG. 7B is an enlarged cross sectional view of the working catheter taken along the line 7B—7B of FIG. 7A as viewed in the direction of the arrows.
Figure 7C:
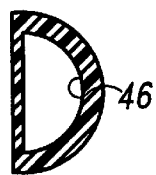
FIG. 7C is an enlarged cross sectional view of the working catheter taken along the line 7C—7C of FIG. 7A as viewed in the direction of the arrows.
Figure 7D:
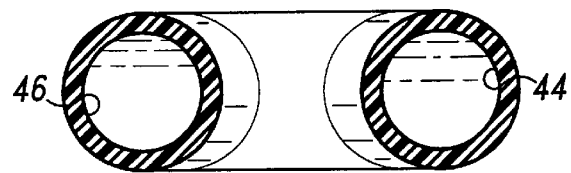
FIG. 7D is an enlarged cross sectional view of the working catheter taken along the line 7D—7D of FIG. 7A as viewed in the direction of the arrows.

In addition, a clamp 62 is positioned on the egress line 47, while a clamp 64 is positioned on the ingress line 45 as shown in FIG. 7A. It should be understood that closure of the clamp 64 causes fluid communication between the first proximal working orifice 48 and the first distal working orifice 50 to be prevented. Similarly, closure of the clamp 62 prevents fluid communication between the second proximal working orifice 52 and the second distal working orifice 54.

The catheter system 12 additionally includes a locking mechanism 56 which is schematically shown in FIG. 3. The locking mechanism 56 operates to lock the working catheter 42 in relation to the guide catheter 34 at any one of two positions. In particular, the locking mechanism 56 may lock the working catheter 42 relative to the guide catheter 34 in an operative position (see e.g. FIGS. 5, 9, and 11) or in a stowed position (see e.g. FIGS. 3, 4 and 10). It should be noted that when the working catheter 42 is locked in the operative position, (i) the working catheter 42 extends through the guide lumen 36 of the guide catheter 34 and out of the distal guide orifice 40 of the guide catheter 34, and (ii) the first distal working orifice 50 and the second distal working orifice 54 are each positioned outside of the guide catheter 34. On the other hand, when the working catheter 42 is locked in the stowed position, (i) the working catheter 42 extends into the guide lumen 36 of the guide catheter 34, and (ii) the first distal working orifice 50 and the second distal working orifice 54 are each positioned within the guide lumen 36 of the guide catheter 34.

One type of locking mechanism which may be used as the locking mechanism 56 of the present invention is shown in more detail in FIGS. 4, 5, 6A, 6B, 7A, and 8. Reference number 56 will also be used to identify this locking mechanism. In particular, the locking mechanism 56 includes an internally threaded member 66. The internally threaded member 66 is attached to the guide catheter 34 in a manner which allows the internally threaded member to rotate relative to the guide catheter 34 (see FIGS. 6B and 8).

Figure 4:
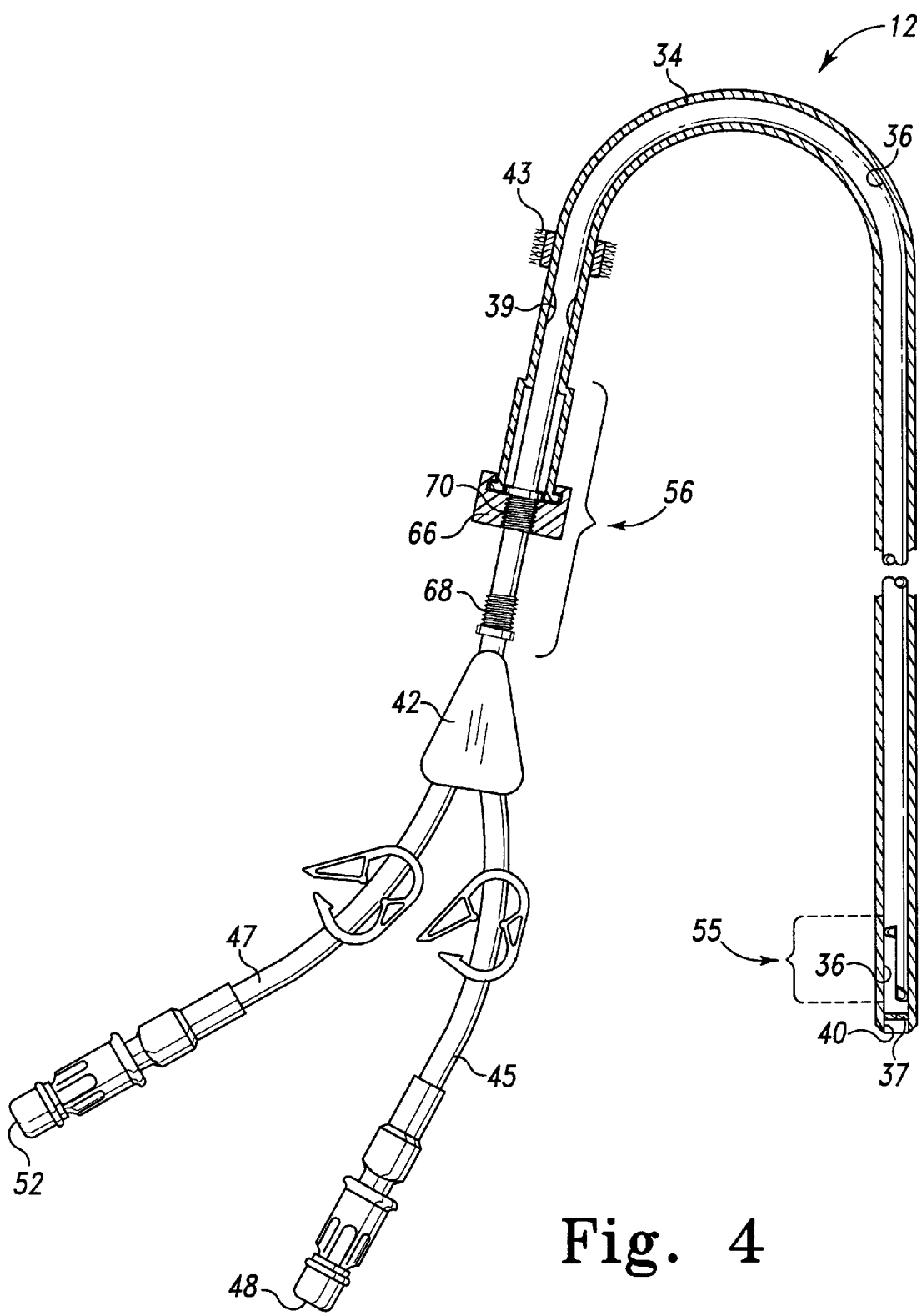
FIG. 4 is a view similar to FIG. 3 but showing one example of a locking mechanism which can be used in the present invention (note that FIG. 4 shows the locking mechanism operating to lock the working catheter in the stowed position)
Figure 5:
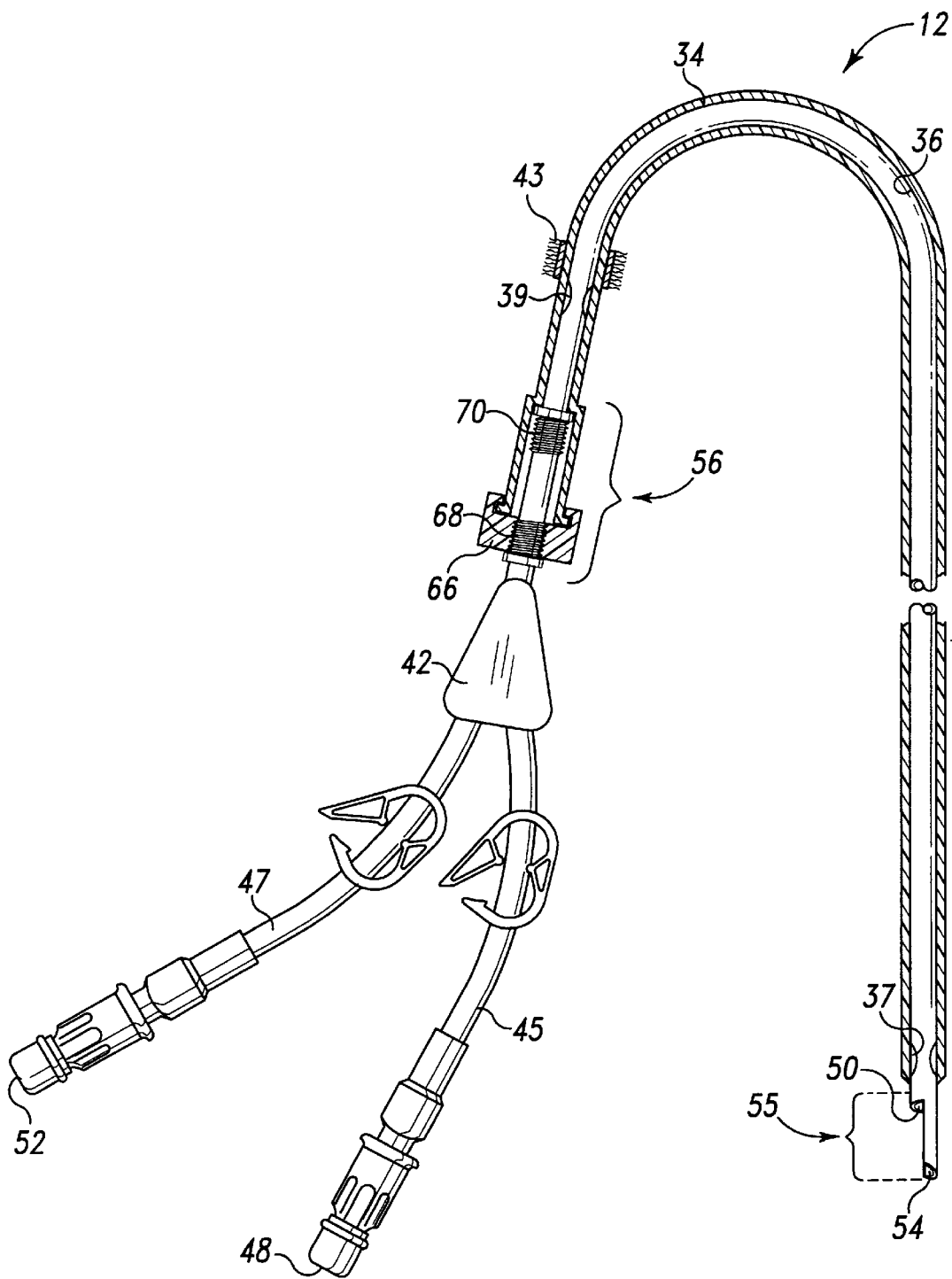
FIG. 5 is a view similar to FIG. 4 but showing the locking mechanism operating to lock the working catheter in the operative position.
Figure 6A:
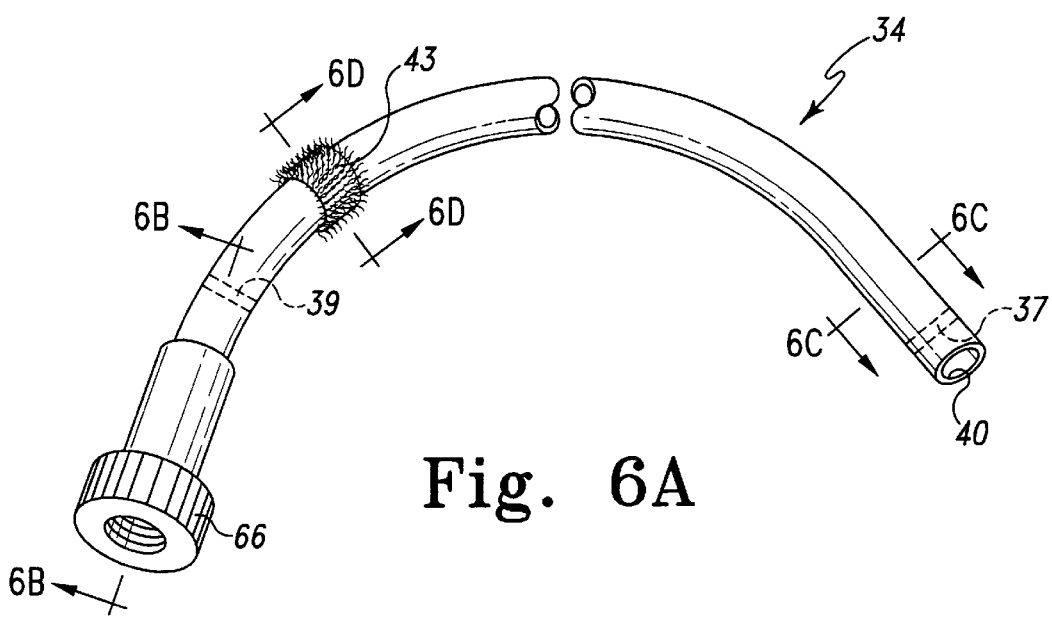
FIG. 6A is an enlarged side elevational view of the guide catheter of the catheter system shown in FIG. 1.
Figure 6B:
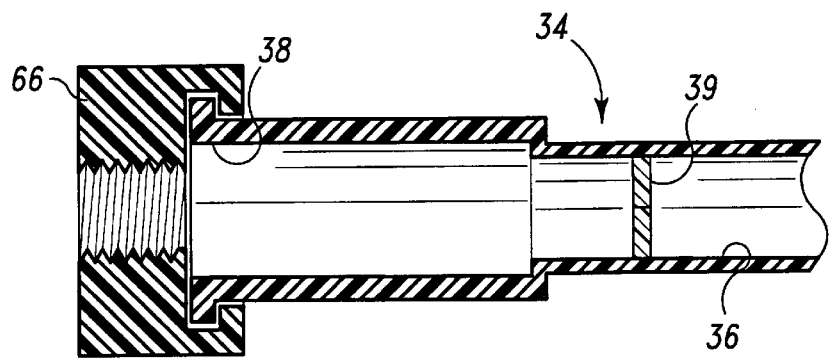
FIG. 6B is an enlarged fragmentary cross sectional view of the guide catheter taken along the line 6B—6B of FIG. 6A as viewed in the direction of the arrows.
Figure 6C:
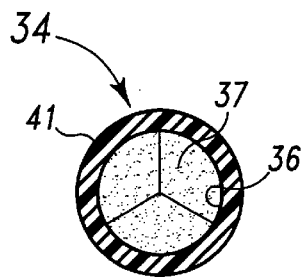
FIG. 6C is an enlarged cross sectional view of the guide catheter taken along the line 6C—6C of FIG. 6A as viewed in the direction of the arrows.
Figure 6D:
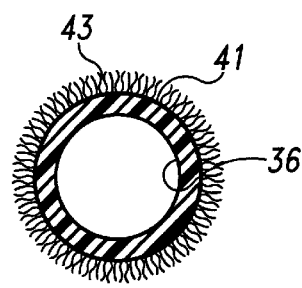
FIG. 6D is an enlarged cross sectional view of the guide catheter taken along the line 6D—6D of FIG. 6A as viewed in the direction of the arrows.
Figure 8:
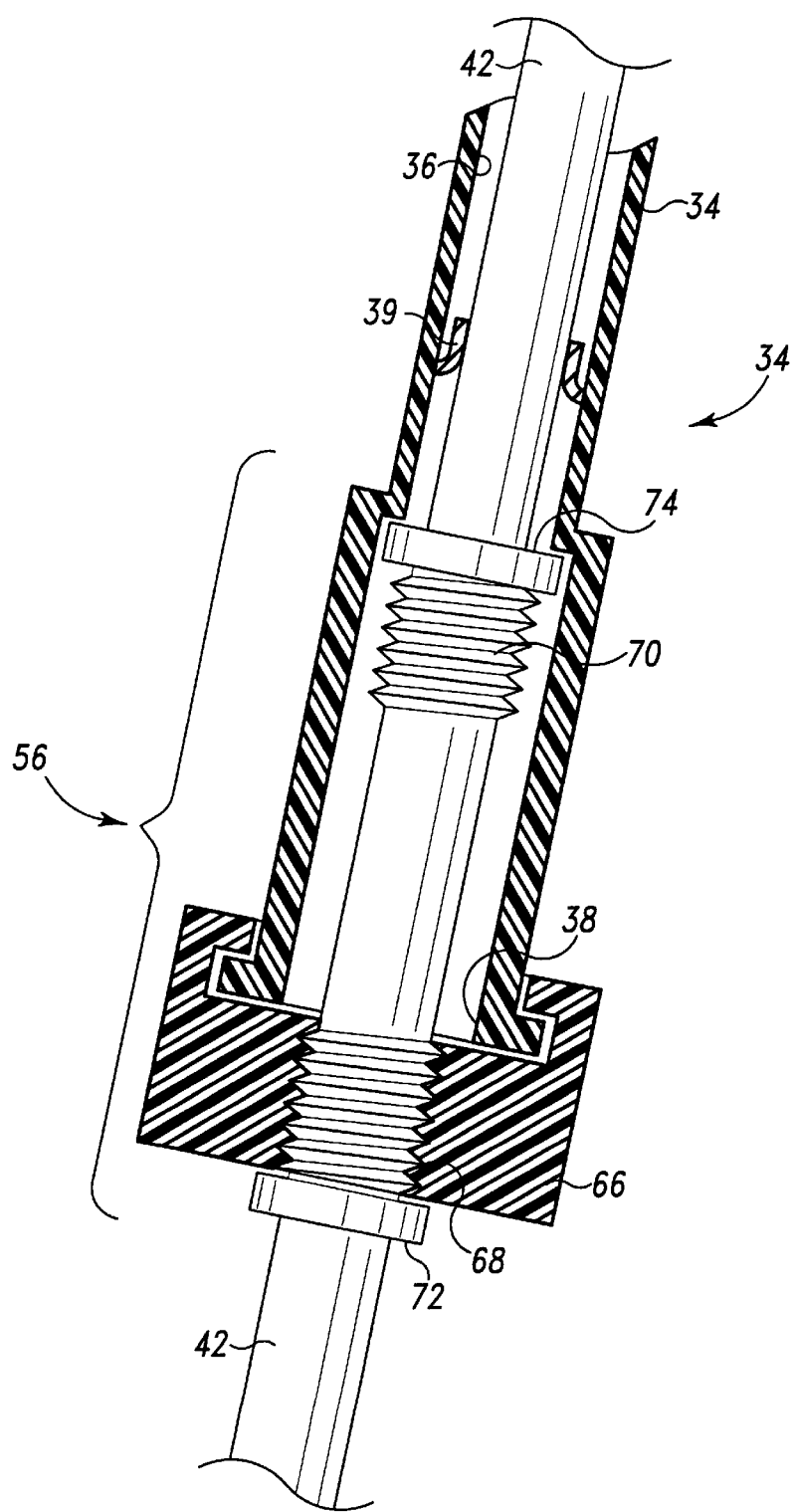
FIG. 8 is an enlarged view of a portion of FIG. 5 which shows the locking mechanism of FIG. 5 in more detail.

The locking mechanism 56 further includes a first set of external threads 68 and a second set of external threads 70 which are each defined in an exterior surface of the working catheter 42. As shown in FIG. 8, the first set of external threads 68 is spaced apart from the second set of external threads 70. The internally threaded member 66 meshes with the first set of external threads 68 so as to lock the working catheter 42 in the operative position as shown in FIG. 5. Similarly, the internally threaded member 66 meshes with the second set of external threads 70 so as to lock the working catheter 42 in the stowed position as shown in FIG. 4.

As further shown in FIG. 8, a proximal stop 72 is provided to limit proximal movement of the internally threaded member 66 relative to the working catheter 42. Similarly, a distal stop 74 is provided to limit distal movement of the internally threaded member 66 relative to the working catheter 42.

While the locking mechanism 56 which is shown in FIGS. 4, 5, 6A, 6B, 7A, and 8 has substantial benefits, numerous other types of locking mechanisms may be used as the locking mechanism 56 (see FIG. 3) and still achieve many of the advantages of the present invention.

For example, another locking mechanism which may be used as the locking mechanism 56 (see FIG. 3) is a detent and groove type locking mechanism (not shown). In particular, such a locking mechanism would include a first groove and a second groove which are (i) spaced apart from each other, and (ii) each defined in an outer surface of the working catheter 42 (the sidewall of the working catheter may need to possess an increased thickness in order to define such grooves therein). A detent (e.g. a ball), supported by the guide catheter 34, may be spring biased into the first groove so as to lock the working catheter 42 in relation to the guide catheter 34 thereby locking the working catheter 42 in the operative position. When desired, the detent may be allowed advance out of the first groove and into the second groove. Thereafter, the detent may be spring biased into the second groove so as to lock the working catheter 42 in relation to the guide catheter 34 thereby locking the working catheter 42 in the stowed position. Examples of detent and groove type locking mechanisms which may be used with some modifications as the locking mechanism 56 of the present invention are disclosed in U.S. Pat. Nos. 4,900,202 and 5,013,194 each issued to Wienhold, and U.S. Pat. Nos. 5,470,180 and 5,779,404 each issued to Jore.

Yet another example of a locking mechanism which may be used as the locking mechanism 56 (see FIG. 3) is a leg and guide channel type locking mechanism (not shown). In particular, such a locking mechanism would include a short leg extending from an outer surface of the working catheter 42. The leg would be fixed in relation to the working catheter 42. The locking mechanism would further include a guide channel defined in a sidewall of the guide catheter 34. The guide channel would extend longitudinally for a short distance (e.g. a few centimeters) along the length of the guide catheter 34. At the proximal end of the guide channel, there would exist a narrowed proximal channel portion of reduced width. Similarly, at the distal end of the guide channel, there would exist a narrowed distal channel portion of reduced width. In operation, the leg would be positioned in the guide channel. If it would be desirable to lock the working catheter 42 in relation to the guide catheter 34 so as to lock the working catheter 42 in the operative position, the working catheter 42 could be advanced distally in relation to the guide catheter 34 until the leg became wedged within the narrowed distal channel portion. A secondary safety latch may be employed to retain the leg in the narrowed distal channel portion. On the other hand, if it would be desirable to lock the working catheter 42 in relation to the guide catheter 34 so as to lock the working catheter 42 in the stowed position, the working catheter 42 could be advanced proximally in relation to the guide catheter 34 until the leg became wedged within the narrowed proximal channel portion. Similarly, another secondary safety latch may be employed to retain the leg in the narrowed proximal channel portion.

Placement of the Catheter System within the Body

The catheter system 12 is placed within the body 14 using the tunneled catheter technique. In particular, a first opening is created by making a small incision in the skin 20 with a scalpel directly over the right internal jugular vein 26. Thereafter, the right internal jugular vein 26 is punctured to create a venotomy 76 (see FIGS. 9–11) at a location directly below the first opening by advancing a needle through the skin incision and the subcutaneous tissue 22 and into the right internal jugular vein 26. Thereafter, a guidewire is advanced through the needle into the right internal jugular vein 26 through the venotomy 76. The needle is then removed over the guidewire. One or more tubular vessel dilators is passed over the guidewire to widen the opening defined in the skin 20 and subcutaneous tissue 22, and further to widen the venotomy 76 defined in the wall of the right internal jugular vein 26 to a caliber similar to that of a tubular guide. Thereafter, the tubular guide is advanced over the guidewire and into the right internal jugular vein 26. Then, a second opening is created in the skin 20 which is spaced apart at least several centimeters from the first opening. A tunneling instrument is advanced from the second opening to the first opening so as to create a passageway within the subcutaneous tissue 22 under the skin 20 between the first opening and the second opening. The catheter system 12 is then advanced into the second opening and through the passageway such that the distal guide orifice 40 of the guide catheter 34 is located adjacent to the first opening. Note that during the above-described advancement of the catheter system 12, the working catheter 42 is locked to the guide catheter 34 in the stowed position (see e.g. FIG. 4).

The distal end of the catheter system 12 is then inserted through the tubular guide member and into the right internal jugular vein 26 so that the tissue ingrowth member 43 is positioned in the subcutaneous tissue 22. Thereafter, the tubular guide member is removed. The first opening is then closed with suture whereby the catheter system 12: (a) is no longer exposed through the first opening, (b) extends for at least several centimeters under the skin 20 between the second opening and the venotomy 76, and (c) extend outs of the second opening so that the proximal end of the catheter system 12 is located outside of the body 14 as shown in FIG. 10.

Figure 10:
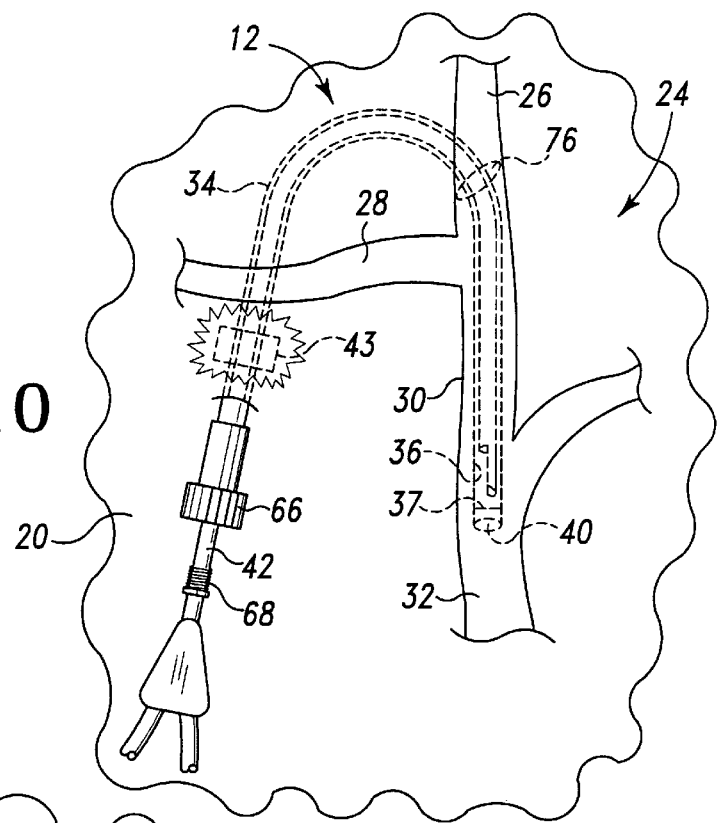
FIG. 10 is a reduced view which is similar to FIG. 9, but showing the working catheter locked to the guide catheter in the stowed position.

Note that after the catheter system 12 is placed in the vascular system 24 as described above, the catheter system 12 is positioned in the right internal jugular vein 26, the right inominate vein 30, and the superior vena cava 32 as shown in FIG. 10. Moreover, note that as the tissue ingrowth member 43 remains in contact with the subcutaneous tissue 22 over a period of time, the subcutaneous tissue 22 becomes affixed to the tissue ingrowth member 43 thereby securing the catheter system 12 to the body 14. As discussed above, affixation of the tissue ingrowth member 43 to the subcutaneous tissue 22 in the above described manner helps prevent bacterial migration up the catheter system 12 from the second opening to the venotomy 76 thereby preventing serious infection.

Performance of a Dialysis Session with the Catheter System

Once the catheter system 12 is placed in the body 14 as described above, the catheter system is positioned as shown in FIG. 10. In this position, the working catheter 42 is locked in the stowed position. When a patient desires to be dialyzed (i.e. engage in a dialysis session), the egress line 47 and the ingress line 45 are respectively connected to the inlet line 16 and the outlet line 18 of the hemodialysis machine 10 as shown in FIG. 1.

Figure 11:
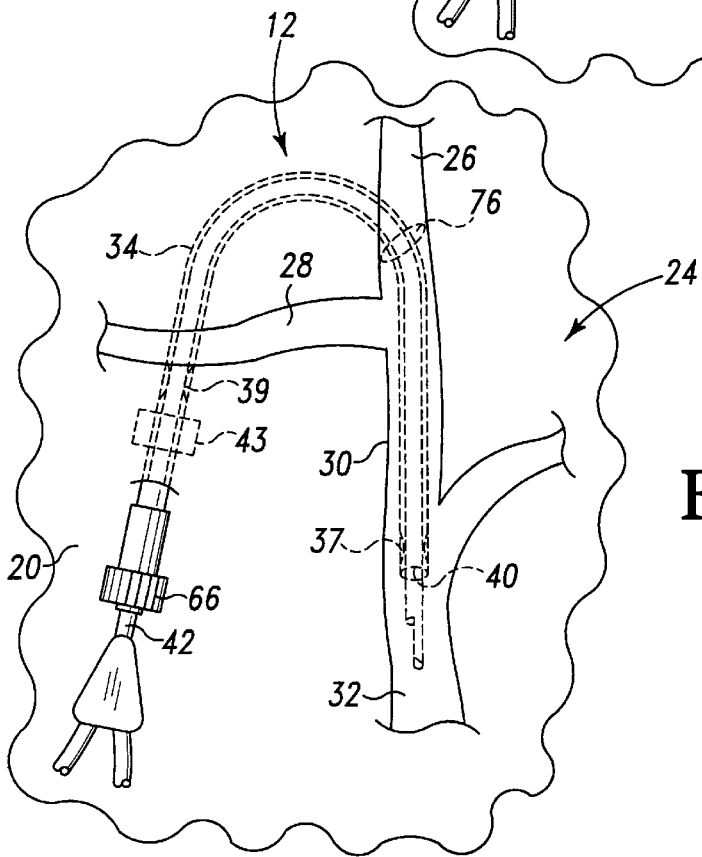
FIG. 11 is a view similar to FIG. 10, but showing the working catheter locked to the guide catheter in the operative position.

Thereafter, the working catheter 42 is unlocked from the guide catheter 34 by rotating the internally threaded member 66 so as to unscrew the internally threaded member 66 out of meshing engagement with the second set of external threads 70 which are defined in the exterior surface of the working catheter 42. The working catheter 42 is then advanced in a proximal direction relative to the guide catheter 34 thereby exposing the distal working segment 55 of the working catheter 42 to the blood flow within the superior vena cava 32. Thereafter, the working catheter 42 is locked to the guide catheter 34 in the operative position as shown in FIG. 11. In particular, the internally threaded member 66 is rotated so as to screw the internally threaded member 66 into meshing engagement with the first set of external threads 68 which are defined in the exterior surface of the working catheter 42.

Moving the working catheter 42 from its stowed position (FIG. 10) to its operative position (FIG. 11), causes the first distal working orifice 50 and the second distal working orifice 54 to be exposed to the blood flow within the superior vena cava 32. With the working catheter 42 locked in the operative position, a dialysis procedure is then performed on the patient's body 14 in a well known manner.

Upon completion of the dialysis procedure, the working catheter 42 is unlocked from the guide catheter 34 by rotating the internally threaded member 66 so as to unscrew the internally threaded member 66 out of meshing engagement with the first set of external threads 68. The working catheter 42 is then advanced in a distal direction relative to the guide catheter 34 thereby withdrawing the distal working segment 55 of the working catheter 42 out of contact with the blood flow in the superior vena cava 32 and into the guide lumen 36 of the guide catheter. Thereafter, the working catheter 42 is locked to the guide catheter 34 in the stowed position thereby assuming the position as shown in FIG. 10. In particular, the internally threaded member 66 is rotated so as to screw the internally threaded member 66 into meshing engagement with the second set of external threads 70.

After the working catheter 42 is locked in its stowed position, the egress line 47 and ingress line 45 are respectively disconnected from the inlet line 16 and the outlet line 18. The proximal orifices 48 and 52 are then each covered with any suitable device (e.g. a cap), and the patient is able to carry on about his/her business. Thereafter, when a patient desires to be dialyzed again, the above procedure is repeated.

With the catheter system 12 of the present invention, it should be appreciated that the length of time which the distal orifices 50, 54 of the working catheter 42 are exposed to the blood flow in the superior vena cava 32 is substantially reduced relative to the length of time which the corresponding distal orifices of conventional hemodialysis catheters are exposed. This reduction in blood flow exposure time substantially reduces the likelihood that the distal orifices 50, 54 will become partially or totally occluded due to attachment or build-up of blood clots, such as fibrin, on the outer and inner surfaces of the distal working segment 55 of the working catheter 42.

In order to further reduce the likelihood that the distal orifices 50, 54 will become partially or totally occluded due to blood clot attachment or build-up, a quantity of blood clot dissolving liquid may be advanced into the catheter system 12 after a dialysis session is completed in order to flush the fluid flow paths of the working catheter 42 and create a pool in which the distal working segment 55 of the working catheter 42 may be bathed. In particular, after the egress line 47 and ingress line 45 are respectively disconnected from the inlet line 16 and the outlet line 18 following completion of dialysis session, a quantity of blood clot dissolving liquid may be advanced into the egress line 47 and/or the ingress line 45. Advancement of the blood clot dissolving liquid into the egress line 47 causes flushing of the following portions of the working catheter 42: (i) the second proximal working orifice 52, (ii) the egress line 47, (iii) the egress lumen 46, and (iv) the second distal working orifice 54. Similarly, advancement of the blood clot dissolving liquid into the ingress line 45 causes flushing of the following portions of the working catheter 42: (i) the first proximal working orifice 48, (ii) the ingress line 45, (iii) the ingress lumen 44, and (iv) the first distal working orifice 50. Advancement of the blood clot dissolving liquid into the catheter system 12 may be continued until substantially all of the blood is removed from (i) the working catheter 42, and (ii) the guide lumen 36 of the guide catheter 34. This may require an amount of the blood clot dissolving liquid to be advanced past the distal valve 37 and out of the distal orifice 40 of the guide catheter 34. Advancement of the blood clot dissolving liquid into the catheter system 12 in the above-described manner causes an amount of the blood clot dissolving liquid to become trapped or pooled within the guide lumen 36 of the guide catheter 34 at a location which is proximal to the distal valve 37 and distal to the proximal valve 39. While the blood clot dissolving liquid is pooled within the guide lumen 36 of the guide catheter 34 at the above-described location, the blood clot dissolving liquid contacts the working catheter 42 at the first distal working opening 50 and the second distal working opening 54. This advantageously helps prevent total or even partial occlusion of the orifices 50, 54 due to blood clot build-up. One type of blood clot dissolving liquid which may be used with the present invention is urokinase.

After the blood clot dissolving liquid is advanced into the catheter system 12 in the above-described manner, then the proximal orifices 48 and 52 are each sealed with any suitable device (such as a cap), and subsequently the patient is able to carry on about his/her business. Thereafter, when a patient desires to be dialyzed again, the above procedure is repeated.

While advancement of the blood clot dissolving liquid (such as urokinase) into the guide lumen 36 of the guide catheter 34 after a dialysis session has been completed has many advantages, some advantages may also be achieved by advancement of an alternative solution into the catheter system 12 after a dialysis session. For example, instead of advancing blood clot dissolving liquid (such as urokinase) into the catheter system 12 after a dialysis session, a heparin lock flush solution may be advanced into the catheter system 12 after a dialysis session has been completed in order to flush the fluid flow paths of the working catheter 42 and create a pool in which the distal working segment 55 of the working catheter 42 may be bathed.

It should be noted that while the distal valve 37 helps maintain the flushing solution (e.g. urokinase or heparin) within the guide lumen 36 of the guide catheter 34 of the catheter system 12 during idle periods when the working catheter is positioned in the stowed position, the distal valve 37 also helps prevent blood which is flowing in the superior vena cava flow from advancing into contact with the distal orifices 50, 54 of the working catheter 42 of the catheter system 12 during idle periods when the working catheter is positioned in the stowed position.

It should further be understood that the distal valve 37 and the proximal valve 39 help prevent blood from escaping through the catheter system 12 during idle periods (i.e. after completion of a dialysis session and before commencement of a subsequent dialysis session). It should also be appreciated that during a dialysis session, the valves 37 and 39 function to prevent blood and/or air leakage through a space defined between the outer surface of the working catheter 42 and the inner surface of the guide catheter 34.

While the invention has been illustrated and described in detail in the drawings and foregoing description, the same is to be considered as illustrative and not restrictive in character, it being understood that only the preferred embodiments and methods have been shown and described and that all changes and modifications that come within the spirit of the invention are desired to be protected.

For instance, while the above-described catheter system 12 was described in relation to the performance of hemodialysis, the catheter system 12 can also be utilized to perform other medical procedures in which dual-lumen catheter access to the central venous system is required. An example of such other medical procedures is plasmapheresis in which blood is withdrawn from the vascular system, components of the blood are separated outside of the body, and a portion of the blood components are then returned to the vascular system.

Moreover, the above-described catheter system utilized to perform hemodialysis (i.e. catheter system 12) can be modified to perform medical procedures in which single-lumen catheter access to the vascular system is required. In particular, the dual lumen working catheter 42 of the catheter system 12 may be modified to be a single lumen catheter, and utilized in a manner similar to that described above with respect to the catheter system 12. Examples of medical procedures in which single-lumen catheter access to the vascular system is required includes (i) chemotherapy or other long-term medicinal infusions, (ii) total parenteral nutrition, (iii) repetitive blood transfusions, and (iv) repetitive blood samplings.

In addition, another medical procedure which may be performed using the above catheter system (i.e. catheter system 12) or the above single-lumen modification of such catheter system is peritoneal dialysis.

There are a plurality of advantages of the present invention arising from the various features of the catheter system described herein. It will be noted that alternative embodiments of the catheter system of the present invention may not include all of the features described yet still benefit from at least some of the advantages of such features. Those of ordinary skill in the art may readily devise their own implementations of the catheter system that incorporate one or more of the features of the present invention and fall within the spirit and scope of the present invention as defined by the appended claims.

What is claimed is:

1. A catheter system, comprising:

a working catheter having a distal working orifice;

a guide catheter having a guide lumen and a distal guide orifice; and a locking mechanism which locks said working catheter relative to said guide catheter in (i) an operative position, and (ii) a stowed position, wherein when said working catheter is locked in said operative position, (i) said working catheter extends through said guide lumen of said guide catheter and out of said distal guide orifice of said guide catheter, and (ii) said distal working orifice of said working catheter is positioned outside of said guide catheter, wherein when said working catheter is locked in said stowed position, (i) said working catheter extends into said guide lumen of said guide catheter, and (ii) said distal working orifice of said working catheter is positioned within said guide lumen of said guide catheter, wherein said locking mechanism includes an internally threaded member attached to said guide catheter, wherein said locking mechanism further includes a first set of external threads and a second set of external threads which are each defined in an exterior surface of said working catheter, wherein said first set of external threads is spaced apart from said second set of external threads, wherein said internally threaded member meshes with said first set of external threads so as to lock said working catheter in said operative position, and wherein said internally threaded member meshes with said second set of external threads so as to lock said working catheter in said stowed position.

2. A method of performing dialysis with a catheter system which includes (i) a working catheter having a distal working orifice, and (ii) a guide catheter having a guide lumen and a distal guide orifice, comprising the steps of:

locking said working catheter in an operative position in which (i) said working catheter extends through said guide lumen of said guide catheter and out of said distal guide orifice of said guide catheter, and (ii) said distal working orifice of said working catheter is positioned outside of said guide catheter;

advancing and withdrawing blood through said working catheter while said working catheter is locked in said operative position; and locking said working catheter in a stowed position in which (i) said working catheter extends into said guide lumen of said guide catheter, and (ii) said distal working orifice of said working catheter is positioned within said guide lumen of said guide catheter;

unlocking said working catheter from said guide catheter after said advancing and withdrawing step, wherein said operative position locking step includes the step of rotating an internally threaded member which is attached to said guide catheter so as to screw said internally threaded member into meshing engagement with a first set of external threads which is defined in an exterior surface of said working catheter, wherein said unlocking step includes the step of rotating said internally threaded member so as to unscrew said internally threaded member out of meshing engagement with said first set of external threads which is defined in said exterior surface of said working catheter, and wherein said stowed position locking step includes the step of rotating said internally threaded member so as to screw said internally threaded member into meshing engagement with a second set of external threads which is defined in said exterior surface of said working catheter.

3. The method of claim 2, wherein said first set of external threads is spaced apart from said second set of external threads.

4. A catheter system, comprising:

a multi-lumen working catheter having a first distal working orifice and a second distal working orifice;

a guide catheter having a guide lumen and a distal guide orifice; and a locking mechanism which locks said working catheter relative to said guide catheter in (i) an operative position, and (ii) a stowed position, wherein when said working catheter is locked in said operative position, (i) said working catheter extends through said guide lumen of said guide catheter and out of said distal guide orifice of said guide catheter, and (ii) said first distal working orifice and said second distal working orifice are each positioned outside of said guide catheter, wherein when said working catheter is locked in said stowed position, (i) said working catheter extends into said guide lumen of said guide catheter, and (ii) said first distal working orifice and said second distal working orifice are each positioned within said guide lumen of said guide catheter, wherein said locking mechanism includes an internally threaded member attached to said guide catheter, wherein said locking mechanism further includes a first set of external threads and a second set of external threads which are each defined in an exterior surface of said working catheter, wherein said first set of external threads is spaced apart from said second set of external threads, wherein said internally threaded member meshes with said first set of external threads so as to lock said working catheter in said operative position, and wherein said internally threaded member meshes with said second set of external threads so as to lock said working catheter in said stowed position.

* * * * *